(12) United States Patent
Friedli et al.

(10) Patent No.: US 11,488,710 B2
(45) Date of Patent: Nov. 1, 2022

(54) METHOD FOR CONTROLLING OPERATION OF A MEDICAL DEVICE IN A MEDICAL SYSTEM AND MEDICAL SYSTEM

(71) Applicant: Roche Diabetes Care, Inc., Indianapolis, IN (US)

(72) Inventors: Kurt Friedli, Mannheim (DE); Michael Mueller, Mannheim (DE); Nils Danckwardt, Mannheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 268 days.

(21) Appl. No.: 16/875,150

(22) Filed: May 15, 2020

(65) Prior Publication Data

US 2020/0279646 A1    Sep. 3, 2020

Related U.S. Application Data

(63) Continuation of application No. PCT/EP2018/081308, filed on Nov. 15, 2018.

(30) Foreign Application Priority Data

Nov. 17, 2017  (EP) .................................... 17202302

(51) Int. Cl.
 *G16H 40/67* (2018.01)
 *A61M 5/142* (2006.01)
 (Continued)

(52) U.S. Cl.
 CPC ............ *G16H 40/67* (2018.01); *A61M 5/142* (2013.01); *G06F 11/0796* (2013.01);
 (Continued)

(58) Field of Classification Search
 None
 See application file for complete search history.

(56) References Cited

U.S. PATENT DOCUMENTS 5,915,082 A    6/1999 Marshall et al.
6,128,774 A   10/2000 Necula et al.
              (Continued)

FOREIGN PATENT DOCUMENTS

JP    2003-520648 A      7/2003
JP    2018025587 A  *   2/2018
                (Continued)

OTHER PUBLICATIONS

English translation for JP 2018-25587A (Year: 2018).*
(Continued)

*Primary Examiner* — Manuel A Mendez
(74) *Attorney, Agent, or Firm* — Bose McKinney & Evans LLP

(57) ABSTRACT

A method for controlling operation of a medical device in a medical system having a medical device, a communication device including a remote control for the medical device, and a safety device adapted for data communication with the communication device. Input data is provided and processed by a first calculation to thereby provide a first calculation result. The input data is processed by a second calculation executed separately from first calculation to thereby provide a second calculation result. The first and second calculation results are compared. When the first and second calculation results are found equal, remote control of the medical device by a medical device application running on the communication device is allowed. When the first and second calculation results are found not equal, the medical device application running on the communication device for remote control of the medical device is prevented.

15 Claims, 8 Drawing Sheets

(51) Int. Cl.
*G06F 11/07* (2006.01)
*G06F 11/16* (2006.01)
*G06F 21/60* (2013.01)

(52) U.S. Cl.
CPC ...... *G06F 11/1637* (2013.01); *G06F 11/1654* (2013.01); *G06F 21/606* (2013.01); *A61M 2205/3553* (2013.01); *A61M 2205/50* (2013.01); *A61M 2209/01* (2013.01)

(56) References Cited

U.S. PATENT DOCUMENTS

| | | |
|---|---|---|
| 2008/0256076 A1 | 10/2008 | Claus et al. |
| 2011/0126188 A1 | 5/2011 | Bernstein et al. |
| 2011/0275410 A1 | 11/2011 | Caffey et al. |
| 2012/0016295 A1 | 1/2012 | Tsoukalis |
| 2012/0066551 A1 | 3/2012 | Palus et al. |
| 2015/0182694 A1 | 7/2015 | Rosinko |
| 2016/0034658 A1 | 2/2016 | Berman et al. |

FOREIGN PATENT DOCUMENTS

| | | |
|---|---|---|
| RU | 164 155 U1 | 8/2016 |
| WO | WO 01/54753 A2 | 8/2001 |

OTHER PUBLICATIONS

International Search Report and Written Opinion of the International Searching Authority, PCT/EP2018/081308, dated Jan. 31, 2019, 11 pages.

Preschern et al., Building a Safety Architecture Pattern System, Pattern Languages of Program, Jul. 2015, 55 pages.

IEC 61508, Functional Safety of Electrical/Electronic/Programmable Electronic Safety-related Systems (E/E/PE, or E/E/PES), https://en.wikipedia.org/w/index.php?title=IEC_61508&oldid=951752716.

IEC 61511, Functional safety—Safety instrumented systems for the process industry sector, https://en.wikipedia.org/w/index.php?title=IEC_61511&oldid=840284566.

\* cited by examiner

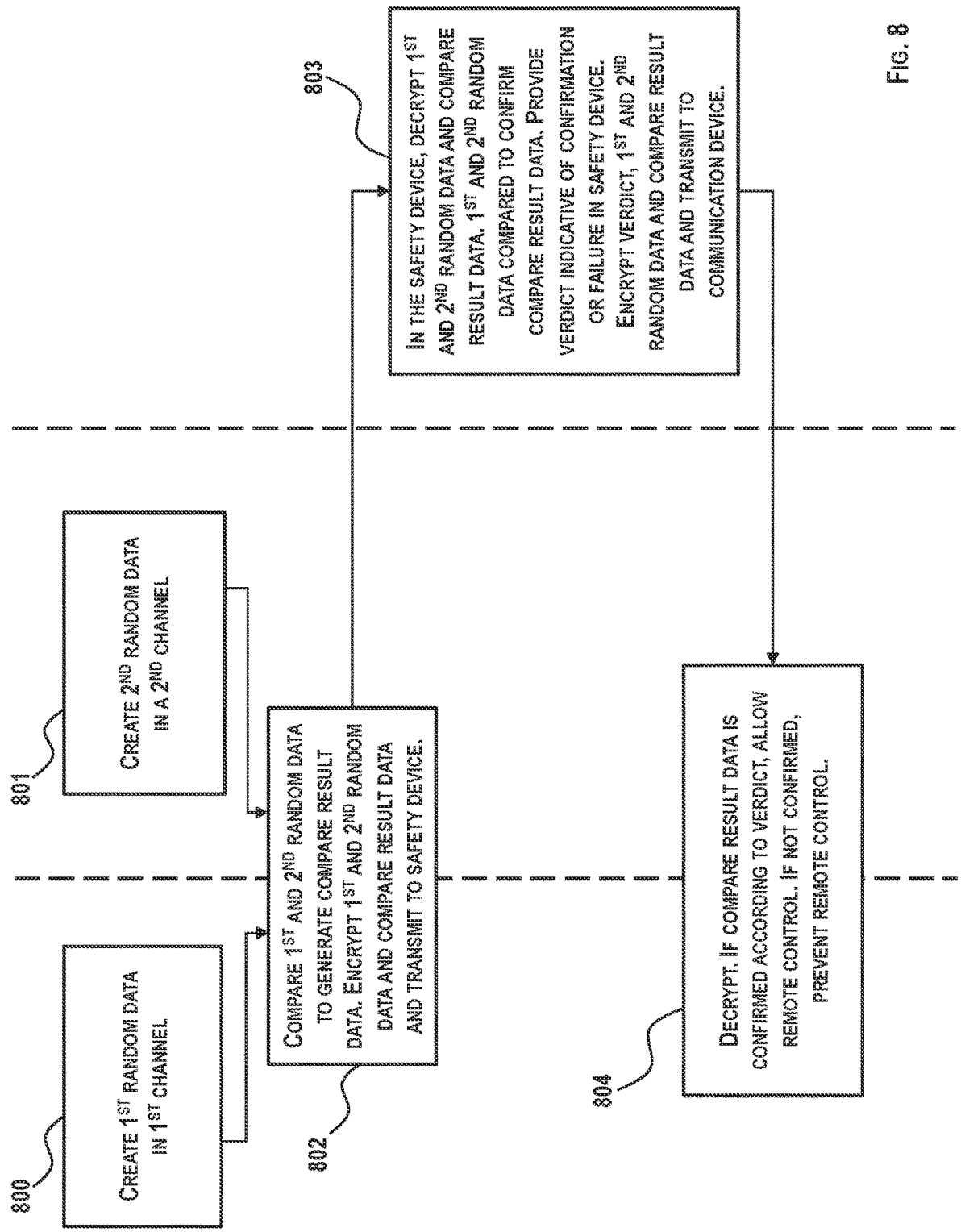

METHOD FOR CONTROLLING OPERATION OF A MEDICAL DEVICE IN A MEDICAL SYSTEM AND MEDICAL SYSTEM

RELATED APPLICATIONS

This application is a continuation of PCT/EP2018/081308, filed Nov. 15, 2018, which claims priority to EP 17 202 302.0, filed Nov. 17, 2017, the entire disclosures of both of which are hereby incorporated herein by reference.

BACKGROUND

The present disclosure refers to a method for controlling operation of a medical device in a medical system and a medical system.

Medical devices in which a malfunction can lead to a hazard to a user of the medical device must adhere to functional safety principles to comply with normative requirements. Non-medical devices do not usually adhere to these principles. If a medical device, for example an insulin infusion pump, is to be controlled by a non-medical device such as a mobile phone, functional safety of the medical device has to be ensured.

U.S. Publication No. 2015/0182694 A1 discloses a safety processor that acts as an intermediary device between a remote control device, such as a smartphone, and a medical device to review transmissions from the smartphone prior to the transmissions being delivered to the medical device. The safety processor can determine whether the smartphone is compatible with the medical device by checking the type and version of the smartphone as well as the versions of the operating software and/or firmware resident on the phone. The safety processor can also check whether the operating command entered into the smartphone is within acceptable parameters.

Systems and methods for remote control and/or wireless (re-)programming of drug pump devices are described in U.S. Publication No. 2011/0275410 A1. In various embodiments, a smartphone or other wireless handheld device is used to send control commands and/or drug-delivery protocols to a wireless receiver of the drug pump device, e.g., via a Wi-Fi, Bluetooth, or near-field communication link. The smartphone may be equipped with a dongle to provide security and/or flexibility in the choice of the data-transfer protocol. Further, the smartphone may store a special software application that enables interaction with the user, and which may have security features that prevent unauthorized operation.

For a safe remote programming of a pump infusion system, U.S. Publication No. 2011/0275410 A1 discloses assigning a predetermined program, comparing a protocol to be programmed with a protocol coming from the pump, eliminating possible errors of non-medically certified intervening devices and means, and executing the programming.

U.S. Pat. No. 6,128,774 describes a computer-implemented method of verifying that untrusted software supplied by a code producer is safe to execute by a code consumer. The method includes the step of defining a safety policy that specifies safe operating conditions of the untrusted software on the code consumer. The method also includes the steps of generating a safety predicate for the untrusted software that determines if execution by the code consumer of the untrusted software will violate said safety policy and generating a safety proof that proves that said safety predicate is valid. The method further includes the step of validating the untrusted software for execution based on said safety proof and said safety predicate.

According to U.S. Publication No. 2011/0126188 A1, methods and articles of manufacture for hosting a safety critical application (SCA) on an uncontrolled data processing device (UDPD) are provided. Various combinations of installation, functional, host integrity, coexistence, interoperability, power management, and environment checks are performed at various times to determine if the safety critical application operates properly on the device. The operation of the SCA on the UDPD may be controlled accordingly.

Methods and systems for validating safety critical applications (SCAs) on uncontrolled data processing devices (UDPDs) are disclosed also in U.S. Publication No. 2016/0034658 A1. Various combinations of checks including validation of safety critical features, validation of SCA-UDPD compatibility, and resource management are executed at various times to ensure the SCA operates properly on the device. The operation of the SCA on the UDPD may be controlled accordingly.

According to U.S. Publication No. 2012/0066551 A1, safe operation in a processor may be verified by making use of an execution trace module that is normally only used for testing and software development. During operation of the processor in the field, a sequence of instructions may be executed the processor. A portion of the execution is traced to form a sequence of trace data. The sequence of trace data is compressed to form a checksum. The checksum is compared to a reference checksum, and an execution error is indicated when the checksum does not match the reference checksum.

A method and system of controlling access to a system in a medical environment is disclosed in U.S. Publication No. 2008/0256076 A1. The method includes calculating a signature value for at least one file usable with the medical system, transferring the calculated signature value to a signature file, and providing at least one signature value in the signature file and at least one associated file to a file system configured to be received by the medical system. At least one signature value and at least one associated file are inspected by the medical system to verify the associated file is a known medical software application asset. The medical system comprises an input/output data port configured to receive the external memory storage device, and an operating system capable of reading medical system data from and writing medical system data to the memory storage device.

A lockstep processor system is known from U.S. Pat. No. 5,915,082, which adds error detection, isolation, and recovery logic to one or more lockstep processor system functions; namely, control outputs, processor inputs, I/O busses, memory address busses, and memory data busses.

SUMMARY

The present disclosure provides a method for controlling operation of a medical device in a medical system that provides enhanced safety and security with regard to operation of and communication in the medical system. A medical system is also disclosed.

According to an aspect, a method for controlling operation of a medical device in a medical system is provided. The medical system includes a medical device, a communication device provided with a medical device application running on the communication device and adapted for remote operation control of the medical device, and a safety device adapted for data communication with the communication device. The method, in the medical system, comprises:

providing input data for a calculation process; processing the input data by the calculation process in a first calculation process in the communication device, thereby, providing first calculation result data; processing the input data by the calculation process in a second calculation process executed separately of the first calculation process, thereby, providing second calculation result data; comparing the first and second calculation result data; if the first and second calculation result data are found equal, allowing remote operation control of the medical device by the medical device application running on the communication device; and if the first and second calculation result data are found not equal, preventing the medical device application running on the communication device from remote operation control of the medical device.

According to another aspect, a medical system is provided. The medical system comprises a medical device, a communication device provided with a medical device application running on the communication device and adapted for remote operation control of the medical device, and a safety device adapted for data communication with the communication device. The system is adapted to provide input data for a calculation process; process the input data by the calculation process in a first calculation process in the communication device, thereby, providing first calculation result data; process the input data by the calculation process in a second calculation process executed separately of the first calculation process, thereby, providing second calculation result data; compare the first and second calculation result data; if the first and second calculation result data are found equal, allow remote operation control of the medical device by the medical device application running on the communication device; and if the first and second calculation result data are found not equal, prevent the medical device application running on the communication device from remote operation control of the medical device.

The first calculation result data and the second calculation result data may also be referred to as the first result data and the second result data, respectively. The safety device may also be referred to as a trusted device.

In general, operational safety of a device may be increased by implementing a diverse redundant architecture. Diverse redundancy is known in the art as such and referenced, for example, in the IEC 61508 and IEC 61511 standards. Diverse redundancy refers to the same task being performed more than once, referred to as redundancy, in separate and different manners, for example using different methodology and/or components, referred to as diversity. One diverse set of means for performing one such task may be referred to as a channel which is separate from a different channel for performing the same task. Separate channels for performing tasks are known in the art as such.

The method may comprise providing the input data for the calculation process in both the communication device and the safety device and processing the input data by the calculation process in the second calculation process in the safety device. The first calculation process and the second calculation process my thereby be performed in two separate devices. If the first and the second calculation result data are found equal, the two separate devices may therefore be found to have produced the same calculation result after the same input data was provided to the two separate devices. If the first and the second calculation result data are found not equal, it may be assumed that at least one of the first calculation process in the communication device and the second calculation process in the safety device has not been performed correctly.

The method may further comprise receiving the input data in a first device of the communication device and the safety device, encrypting the input data in the first device, transmitting the encrypted input data from the first device to a second device of the communication device and the safety device, and decrypting the encrypted input data in the second device. For example, the input data may be received and encrypted in the communication device. The encrypted input data may then be transmitted to the safety device and be decrypted in the safety device.

Additionally or as an alternative, a software application for implementing the calculation process may be received in a first device of the communication device and the safety device and may be transmitted from the first device to a second device of the communication device and the safety device. The software application may be stored in at least one of a memory and a storage device of the first device and/or the second device. Additionally, the software application may be encrypted in the first device. The encrypted software application may then be transmitted from the first device to the second device and be decrypted in the second device.

The method may comprise providing the input data for the calculation process in the communication device and processing the input data by the calculation process in the second calculation process in the communication device. The first calculation process may be performed in a first channel of the communication device and the second calculation process may be performed in a second channel of the communication device independent of the first channel. If the first and the second calculation result data are found not equal, it may be assumed that at least one of the first calculation process in the first channel of the communication device and the second calculation process in the second channel of the communication device has not been performed correctly.

The method may comprise providing the first and second calculation result data in the safety device and comparing the first and second calculation result data in the safety device. Providing the first and second calculation result data in the safety device may comprise transmitting the first and/or the second calculation result data from the communication device to the safety device.

The method may further comprise providing compare result data in the safety device, the compare result data indicative of the result of comparing the first and second calculation result data, and transmitting the compare result data from the safety device to the communication device. The compare result data may be encrypted in the safety device. The encrypted compare result data may be transmitted from the safety device to the communication device and be decrypted in the communication device. Compare result data may be any data indicative of the result of comparing the first and second calculation result data. For example, compare result data may consist of a single bit transmitted in a data packet, the single bit indicating whether the first and second calculation result data are found equal or not equal. Alternatively, compare result data may comprise additional information, for example the first and second calculation result data. Compare result data may be indicative of a permission for or a denial of remote operation control of the medical device by the medical device application running on the communication device.

In embodiments in which the first calculation process is performed in the communication device, the second calculation process is performed in the safety device, and comparing the first and second calculation result data is performed in the safety device, the method may comprise encrypting the first result data in the communication device, transmitting the encrypted first result data from the communication device to the safety device, and decrypting the encrypted first result data in the safety device.

In embodiments in which the first calculation process and the second calculation process are performed in the communication device and compare result data is provided in the safety device and transmitted from the safety device to the communication device, the method may comprise encrypting the first and second result data in the communication device, transmitting the encrypted first and second result data from the communication device to the safety device, and decrypting the encrypted first and second result data in the safety device.

The first and second calculation result data may be compared in the communication device. Comparing the first and second calculation result data in the communication device may be in addition or as an alternative to comparing the first and second calculation result data in the safety device.

In embodiments in which the first calculation process is performed in the communication device, the second calculation process is performed in the safety device, and comparing the first and second calculation result data is performed in the communication device, the method may comprise encrypting the second result data in the safety device, transmitting the encrypted second result data from the safety device to the communication device, and decrypting the encrypted second result data in the communication device.

The safety device may be selected from the following group: memory card such as SD card; NFC beacon; remote server device; further medical device different from the medical device. The safety device may be a medical device or a non-medical device. The safety device may be provided with a diverse redundant architecture.

For example, the safety device may be a medical device SD card provided with additional functionality in comparison to a standard SD card, which is known in the art as such. The medical device SD card may be connected to the communication device, for example a mobile phone, like a standard SD card and provide the functionality of a standard SD card, such as file services. Additionally, a safe medical comparison/calculation application, providing additional functionality referred to above with reference to the safety device, may be running on an internal microcontroller of the medical device SD card. The medical device SD card may be configured to perform any or all tasks referred to above with regard to the safety device in a diverse redundant manner.

Alternatively, the safety device may be any other device that may be physically connected to the communication device, for example a USB dongle. The USB dongle or other device that may be physically connected to the communication device may provide the functionality described above with regard to the medical SD card.

The safety device may be a device capable of connecting wirelessly to the communication device via near field communication (NFC). NFC is known as such. The safety device may be an NFC beacon that may be attached directly to the communication device. For example, the safety device may be an NFC sticker or a slim NFC-capable device that is small enough to not hinder normal use of the communication device when attached to the communication device.

The method may comprise providing the calculation process and the comparing of the first and second calculation result data as safety elements of a single fault safety architecture. In a single fault safety architecture, an unwanted result, such as a hazard to a user, does not occur even if one (single) fault occurs within the architecture. For example, a hazard to a user of the medical device may be prevented by preventing the medical device application running on the communication device from remote operation control of the medical device if the first and second calculation result data are found not equal when one of the first and second calculation result data is incorrect due to a fault occurring.

The method may comprise storing, in a memory device provided in at least one of the communication device and the safety device, at least one of the following: the input data; the encrypted input data; the first result data; the encrypted first result data; the second result data; and the encrypted second result data.

For example, the encrypted input data, the encrypted first result data and the encrypted second result data may be stored in a memory device of the safety device. The encrypted input data, the encrypted first result data and the encrypted second result data may then be decrypted and the input data, the first result data and the second result data may be stored in the memory device of the safety device. The input data, the first result data and/or the second result data may then be used for comparing the first and second result data. In the same manner, additionally or as an alternative, data may be stored in a memory device of the safety device and used for comparing the first and second result data.

Input reference data may be provided in at least one of the safety device and the communication device. The input reference data may be compared, in at least one of the safety device and the communication device, to the input data to determine whether the input data is valid input data. If the input data is found valid, remote operation control of the medical device by the medical device application running on the communication device may be allowed. If the input data is found not valid, the medical device application running on the communication device may be prevented from remote operation control of the medical device. The comparing the input data to the reference input data may be performed before or after the comparing the first and second calculation result data or, at least partially, at the same time.

The communication device on which the medical device application is running may be any communication device, for example a mobile communication device, such as a mobile phone, a smart watch, a (mobile) computer, or a portable display device. The communication device may be provided with communication functionality. The communication device may be connected, wirelessly or via a wire, to the medical device and/or the safety device.

The medical device may be an insulin pump. Alternatively, the medical device may be a pen device for administering insulin to a patient. As a further alternative, the medical device may be a glucose monitoring device which may be a glucose monitoring device adapted for continuous glucose monitoring or non-continuous glucose monitoring.

A glucose monitoring device adapted for continuous blood glucose monitoring may be provided with a sensor that is a fully or partially implanted sensor for continuous glucose monitoring (CGM). In general, in the context of CGM, an analyte value or level indicative of a glucose value or level in the blood may be determined. The analyte value may be measured in an interstitial fluid. The measurement may be performed subcutaneously or in vivo. CGM may be implemented as a nearly real-time or quasi-continuous monitoring procedure frequently or automatically providing/updating analyte values without user interaction. In an alternative embodiment, analyte may be measured with a biosensor in a contact lens through the eye fluid or with a biosensor on the skin via transdermal measurement in sudor. A CGM sensor may stay in place for several days to weeks and then must be replaced.

The trusted device may be a device that is known by a provider of the medical device application to work safely. For example, the trusted device may have been confirmed by the provider of the medical device application to perform operations necessary for remote control operation of the medical device correctly under all anticipated operation conditions.

With regard to the medical system, the alternative embodiments described above may apply mutatis mutandis.

In the medical system, the safety device may be an integrated device of the medical device. For example, the safety device may be a memory device, such as an SD card, provided in the medical device. Alternatively, the safety device may comprise at least one of hardware components and software components provided in the medical device and separate from other components of the medical device.

Again, in the method and in the medical system as described above, the communication device may be a hardware device suitable for running a medical device application thereon and separate from the medical device for remote controlling the medical device. Vice versa, the medical device may be a hardware device separate from the communication device. The communication device and the medical device may be configured to communicate with each other, in particular for remote controlling the medical device.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein:

FIG. 8 is a flow diagram for steps of a further method for controlling operation of a medical device in a medical system.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
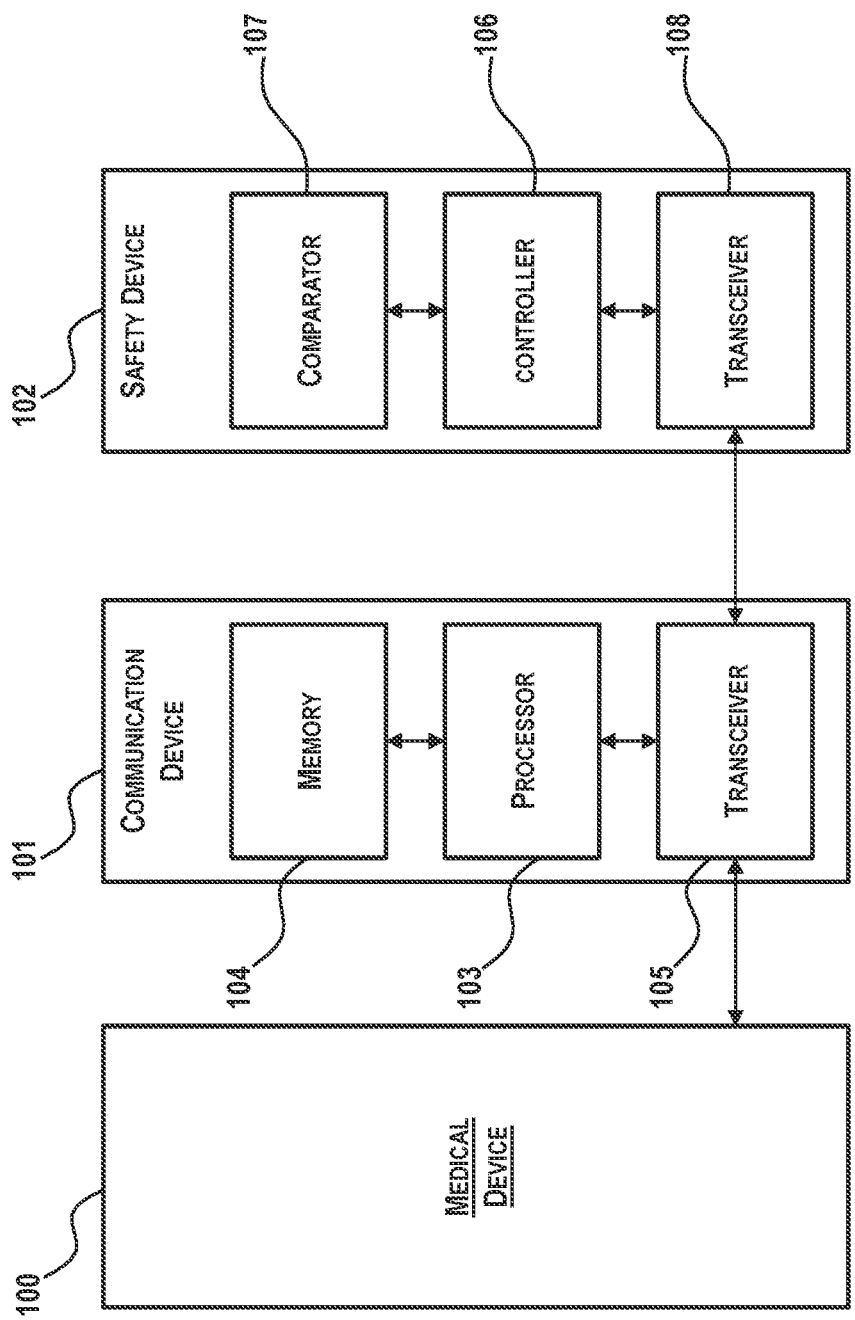
FIG. 1 is a schematic representation of a medical system.

FIG. 1 shows a schematic representation of a medical system comprising a medical device 100, a communication device 101 and a safety device 102. The communication device 101 (also referred to herein as "communication hardware") comprises a processing device 103 (also referred to as a "processor"), a memory device 104 (also referred to as a "memory") and a transceiver 105. The safety device 102 comprises a control device 106 (also referred to as a "controller"), a trusted comparator 107 and a transceiver 108. The medical device 100 may comprise any elements necessary for the desired function of the medical device 100. In the embodiment shown, the medical device 100 is an insulin pump that is configured to be controlled by a medical device application running on the communication device 101. In alternative embodiments, the medical device 100 may be any medical device that may be controlled via the communication device 101. An exemplary embodiment of a medical device 100 is described below with reference to FIG. 3.

The processing device 103 of the communication device 101 is configured to establish a connection to the medical device 100 via the transceiver 105 of the communication device 101. The transceiver 105 of the communication device 101 is configured for a wireless data connection to the medical device 100. The processing device 103 of the communication device 101 is further configured to establish a connection to the safety device 102 via the transceiver 105 of the communication device 101 and the transceiver 108 of the safety device 102. In the embodiment shown, the transceiver 105 of the communication device 101 and the transceiver 108 of the safety device 102 are configured for a wireless data connection between the communication device 101 and the safety device 102.

The processing device 103 of the communication device 101 is configured to execute a medical device application stored in the memory device 104. The control device 106 (also referred to as "controller") of the safety device 102 is configured to receive and transmit data via the transceiver 108 of the safety device 102. The control device 106 is further configured to control the trusted comparator 107. The trusted comparator 107 is configured to receive data from the control device 106, to perform steps of a method for controlling operation of the medical device 100, as laid out in more detail below with reference to FIGS. 4 to 8, and to transmit data to the control device 106.

Figure 2:
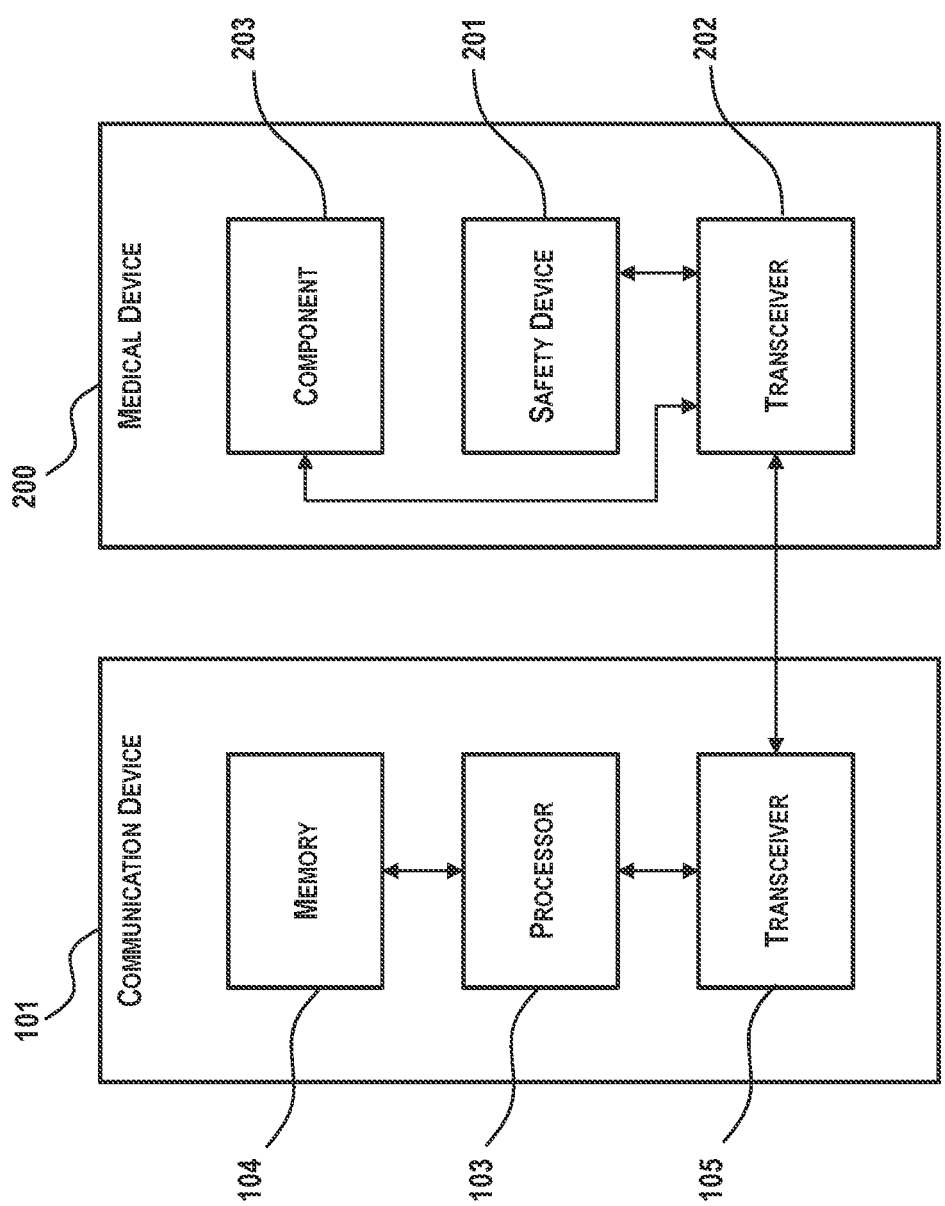
FIG. 2 is a schematic representation of a further medical system.

FIG. 2 shows a schematic representation of a different embodiment of a medical system. The medical system shown in FIG. 2 comprises a communication device 101 and a medical device 200. The communication device 101 corresponds to the communication device 101 shown in FIG. 1. The medical device 200 comprises a safety device 201 and a transceiver 202. The safety device 201 is provided as an integrated device of the medical device 200 and is configured to establish a connection to the communication device 101 via the transceiver 202 of the medical device 200. The transceiver 202 of the medical device 200 is configured for a wireless data connection to the transceiver 105 of the communication device 101. The safety device 201 comprises a control device and a trusted comparator (not shown) corresponding to the control device 106 and the trusted comparator 107 of the safety device 102 show in FIG. 1.

The medical device 200 comprises at least one further component 203 necessary for the desired function of the medical device 200. In the embodiment shown, the medical device 200 is an insulin pump that is configured to be controlled by a medical device application running on the communication device 101 and the at least one further component 203 is configured to provide the insulin pump functionality of the medical device 200. The processing device 103 of the communication device 101 is configured to establish a connection to the at least one further component 203 of the medical device 200 via the transceiver 105 of the communication device 101 and the transceiver 202 of the medical device 200 for controlling the medical device 200 by the medical device application.

Figure 3:
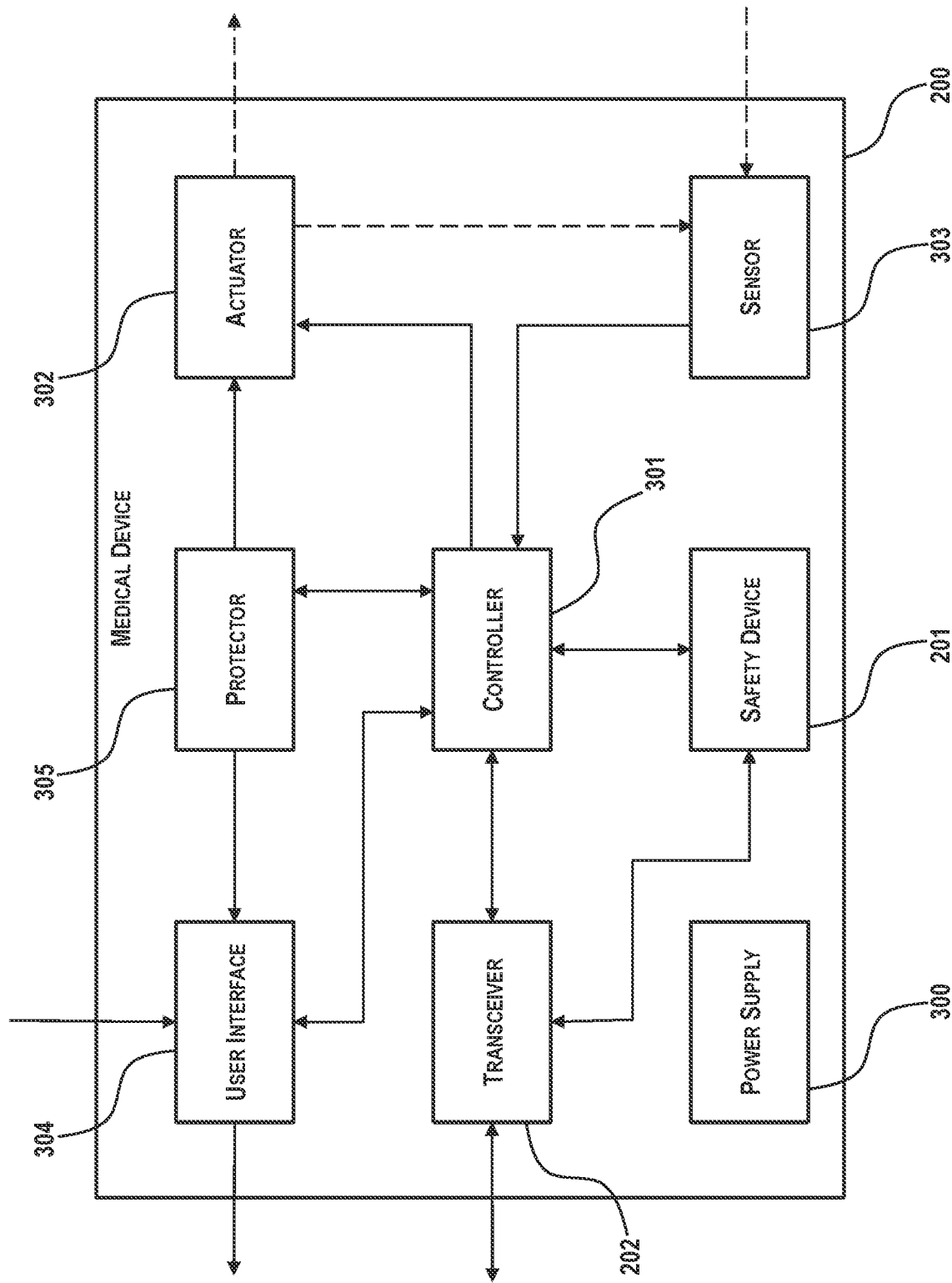
FIG. 3 is a schematic representation of a medical device.

FIG. 3 shows a schematic representation of an embodiment of a medical device 200 which, in the embodiment shown, is an insulin infusion pump. The medical device 200 comprises a power supply 300, configured to supply power to the medical device 200, and a control unit 301, configured to control function of the medical device 200. The control unit 301 (also referred to as a "controller") is functionally connected to a transceiver 202 for data communication with devices external to the medical device 200, for an example, a communication device 101. A safety device 201 is also functionally connected to the transceiver 202 for data communication with devices external to the medical device 200, in particular a communication device 101. The control device 301 controls the function of the safety device 201. A trusted comparator (not shown) provided in the safety device is functionally separate from other components of the medical device 200, including the control device 301.

The control device 301 further controls the insulin infusion pump provided by the medical device 200. An actuator unit 302 comprises at least one actuator, for example a pump, for administering insulin to a user of the medical device 200. A sensor unit 303 comprises at least one sensor. For example, the sensor unit 303 may comprise a pressure sensor configured to measure a pressure in a reservoir containing insulin to be administered to a user of the medical device 200. The medical device 200 further comprises a user interface 304 configured for receiving user input, for example via a touchscreen and/or buttons of the user interface 304, and to transmit signals to a user of the medical device 200. Signals transmitted to a user of the medical device 200 may include visual, acoustic and/or tactile signals. For example, the user interface 304 may comprise a display, a loudspeaker and/or a vibration device for transmitting visual, acoustic and tactile signals, respectively.

A protection unit 305 (also referred to as "protector") enables and/or disables functioning of the actuator unit 302, thereby allowing or preventing administration of insulin to a user of the medical device 200. The protection unit 305 is configured to provide, via the user interface 304, user feedback to a user of the medical device 200 regarding the allowing and/or the preventing of administration of insulin. The protection unit 305 enables and/or disables functioning of the actuator unit 302 based on data and/or commands received from the control unit 301. Data and/or command provided to the protection unit 305 by the control unit 301 may be based, at least in part, on data and/or commands received in the control unit 301 from the safety device 201.

Figure 4:
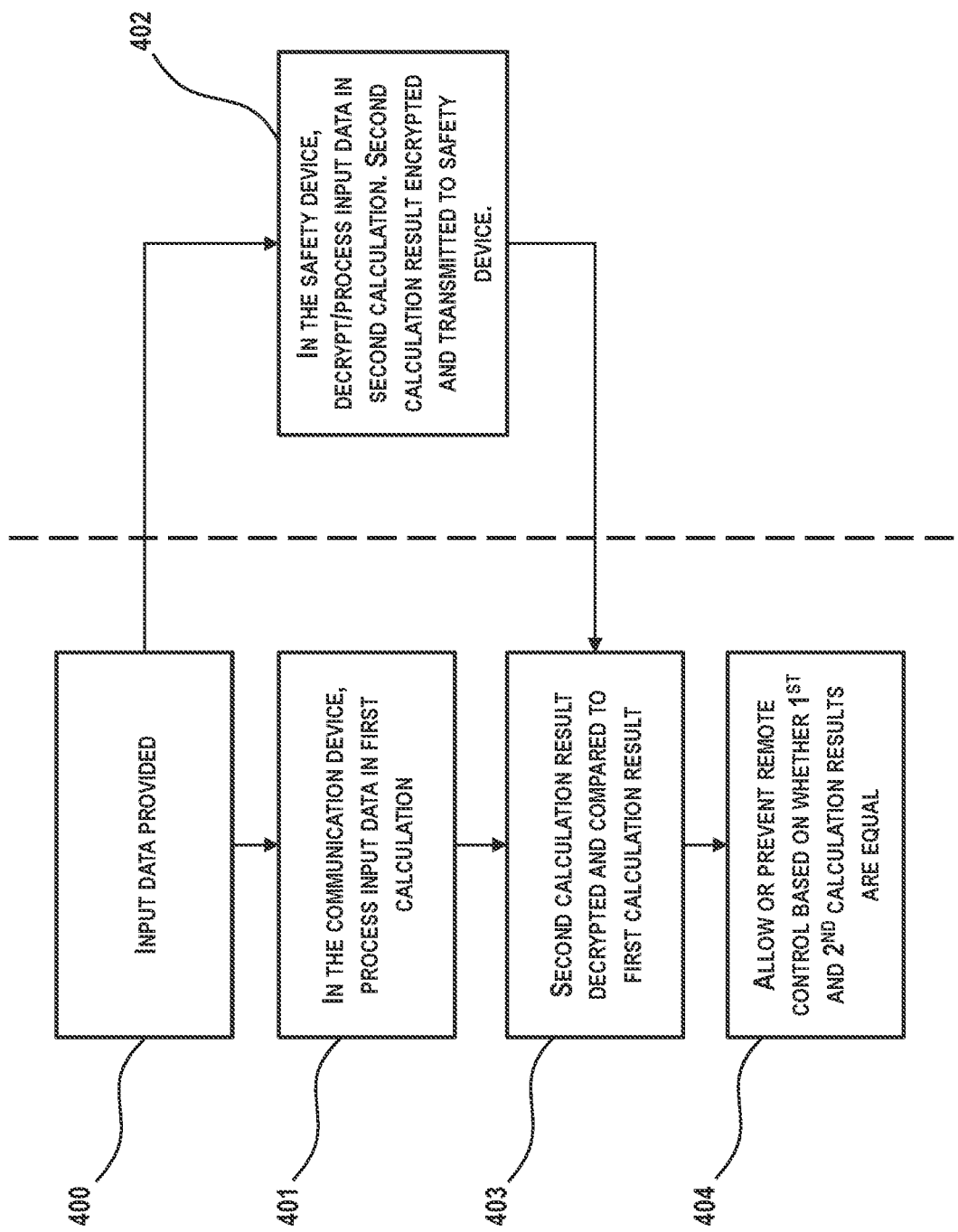
FIG. 4 is a flow diagram for steps of a method for controlling operation of a medical device in a medical system.

FIG. 4 shows steps of a method for controlling operation of a medical device 100 in a medical system in a flow diagram. In step 400 of the method, input data is provided in a medical device application running on a communication device 101, the medical device application adapted for remote operation control of the medical device 100. For example, the input data may be provided by user input in the communication device 101. Alternatively, input data may be received in the communication device 101 via data communication. As a further alternative, input data may be provided as a result of an operation, for example a calculation operation, in the communication device 101. The input data is encrypted in the communication device 101 and transmitted to a safety device 102.

Following, in step 401, the input data is processed in the communication device 101 in a first calculation process (first calculation) resulting in first calculation result data (first calculation result). In step 402, in the safety device 102, the input data is decrypted and processed in a second calculation process (second calculation) resulting in second calculation result data (second calculation result). The second calculation result data is encrypted and transmitted from the safety device 102 to the communication device 101. Steps 401 and 402 may be executed in any order or in parallel.

The second calculation result data is decrypted and compared to the first calculation result data in the communication device 101 in step 403. In step 404, if the first and second calculation result data are found equal, remote control operation of the medical device 100 by the communication device 101 is allowed. On the other hand, if the first and second calculation result data are found not equal, remote control operation of the medical device 100 by the communication device 101 is prevented in step 404.

Figure 5:
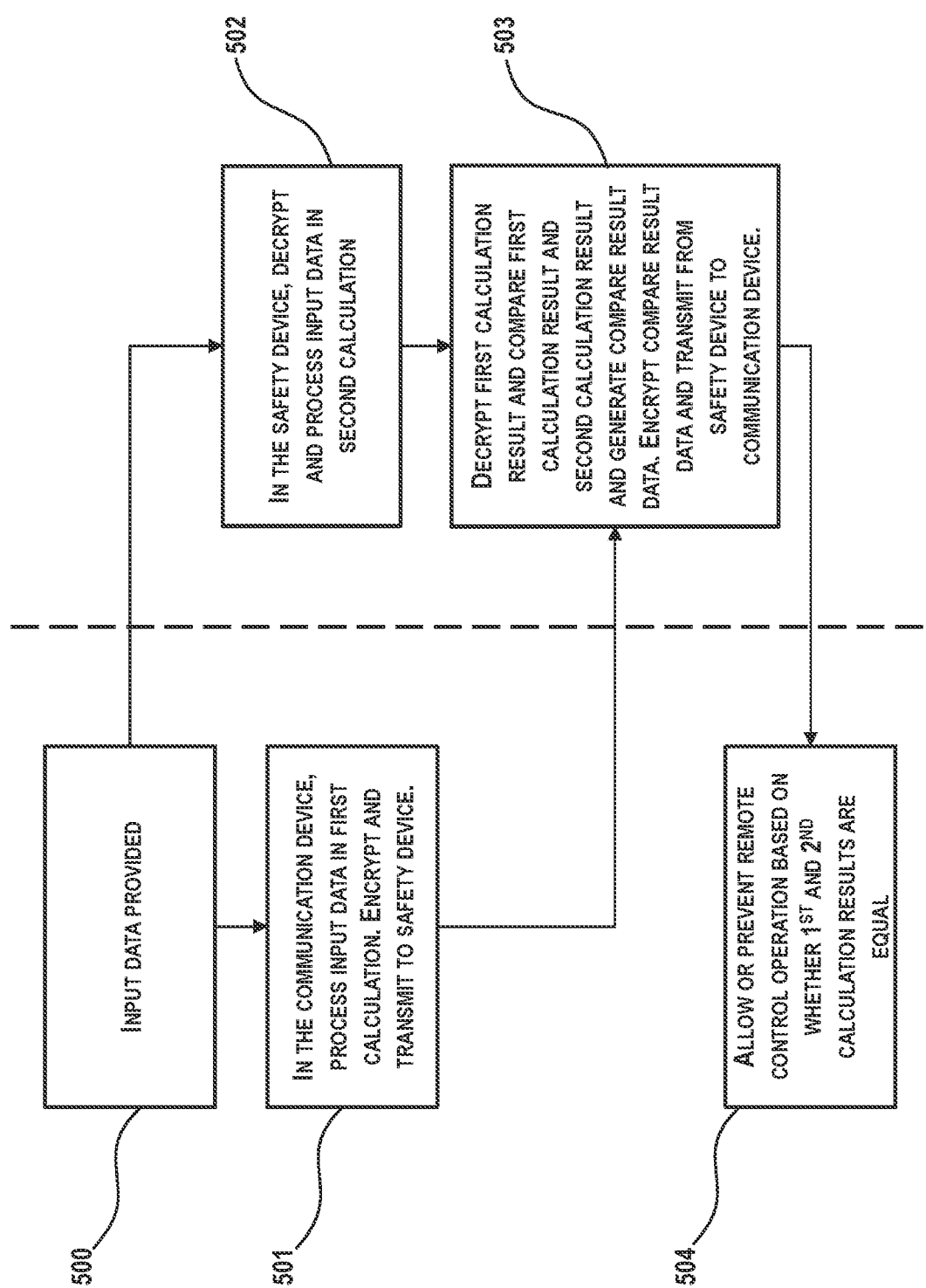
FIG. 5 is a flow diagram for steps of a further method for controlling operation of a medical device in a medical system.

FIG. 5 shows steps of a different embodiment of a method for controlling operation of a medical device 100 in a medical system further comprising a communication device 101 and a safety device 102. Step 500 corresponds to step 400 described with reference to FIG. 4 above. In step 501, the input data is processed in the communication device 101 in a first calculation process resulting in first calculation result data. The first calculation result data is encrypted and transmitted from the communication device 101 to the safety device 102. In step 502, in the safety device 102, the input data is decrypted and processed in a second calculation process resulting in second calculation result data. Steps 501 and 502 may be executed in any order or in parallel.

The first calculation result data is decrypted and compared to the second calculation result data in the safety device 102 in step 503 resulting in compare result data indicative of the result of comparing the first and second calculation result data. The compare result data is encrypted and transmitted from the safety device 102 to the communication device 101. In step 504, the compare result data is decrypted in the communication device 101 and, if the first and second calculation result data are found equal, remote control operation of the medical device 100 by the communication device 101 is allowed. On the other hand, if the first and second calculation result data are found not equal, remote control operation of the medical device 100 by the communication device 101 is prevented in step 504.

Figure 6:
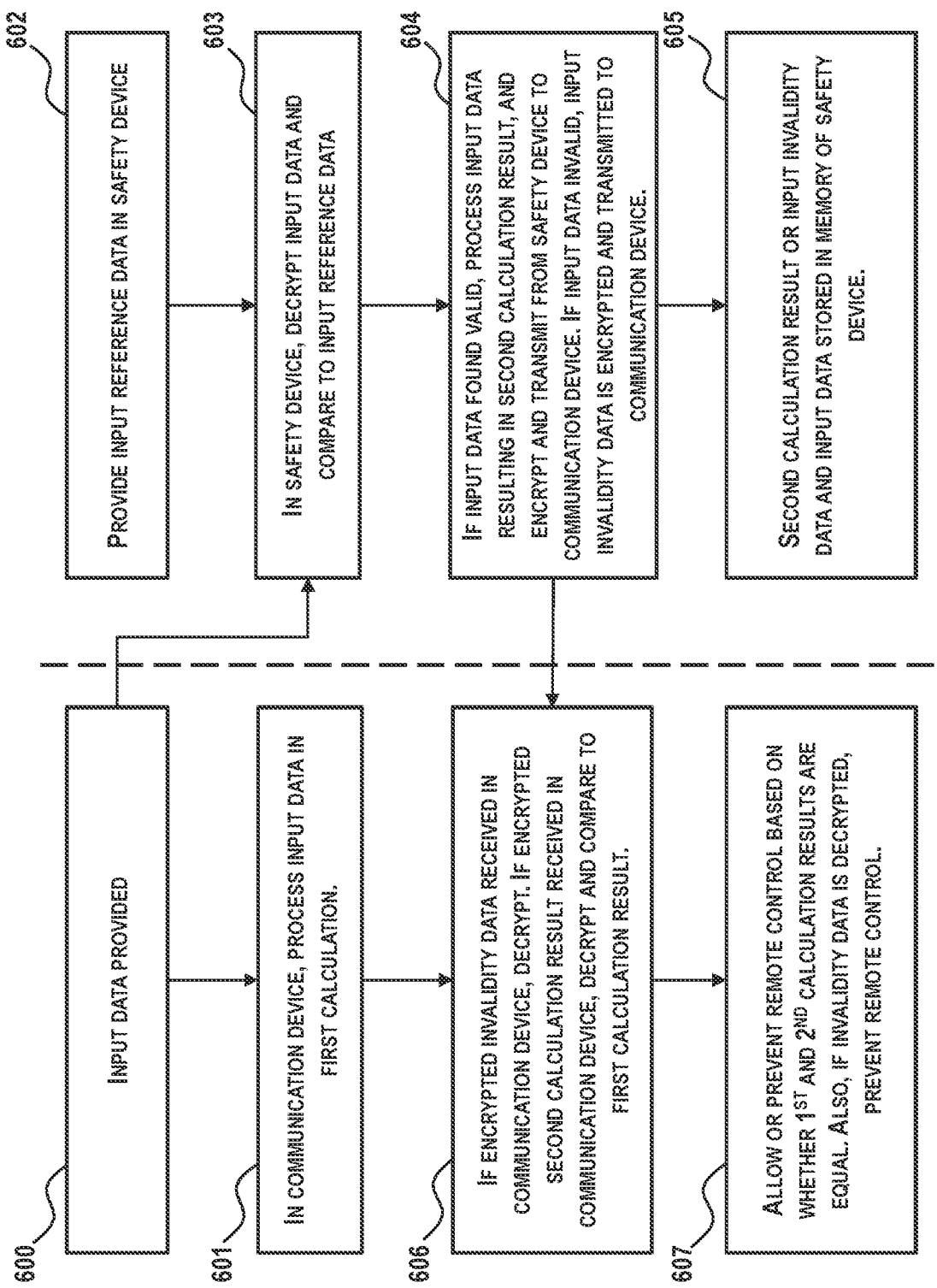
FIG. 6 is a flow diagram for steps of a further method for controlling operation of a medical device in a medical system.

FIG. 6 shows steps of a different embodiment of a method for controlling operation of a medical device 100 in a medical system further comprising a communication device 101 and a safety device 102. In step 600, input data is provided in a medical device application running on a communication device 101. Step 600 corresponds to steps 400 and 500 described above with reference to FIGS. 4 and 5, respectively. In step 601, corresponding to step 401 described with reference to FIG. 4 above, the input data is processed in the communication device 101 in a first calculation process resulting in first calculation result data.

In step 602, input reference data is provided in the safety device 102. The input reference data is indicative of valid input data. In step 603, in the safety device 102, the input data is decrypted and compared to the input reference data. In step 604, if the input data is found to be valid in step 603, the input data is processed in a second calculation process resulting in second calculation result data. The second calculation result data is encrypted and transmitted from the safety device 102 to the communication device 101. If in step 603 the input data is found to be not valid, input invalidity data is provided and encrypted in step 604 and transmitted from the safety device 102 to the communication device 101. In step 605, the second calculation result data or the input invalidity data as well as the input data are stored in a memory of the safety device 102. Additionally, the input reference data and/or any other data relevant to the processes described with reference to FIG. 6 may be stored in the safety device 102.

Steps 600 and 602 may be executed in any order or in parallel. Further, Step 601 may be executed before or after each of steps 603 and 604 or in parallel, at least partially.

In step 606, if encrypted input invalidity data is received in the communication device 101, the input invalidity data is decrypted. Following, remote control operation of the medical device 100 by the communication device 101 is prevented in step 607.

If encrypted second calculation result data is received in the communication device 101, the encrypted second calculation result data is decrypted and compared to the first calculation result data in the communication device 101 in step 606. Following, in step 607, if the first and second calculation result data are found equal, remote control operation of the medical device 100 by the communication device 101 is allowed. On the other hand, if the first and second calculation result data are found not equal, remote control operation of the medical device 100 by the communication device 101 is prevented in step 607.

Figure 7:
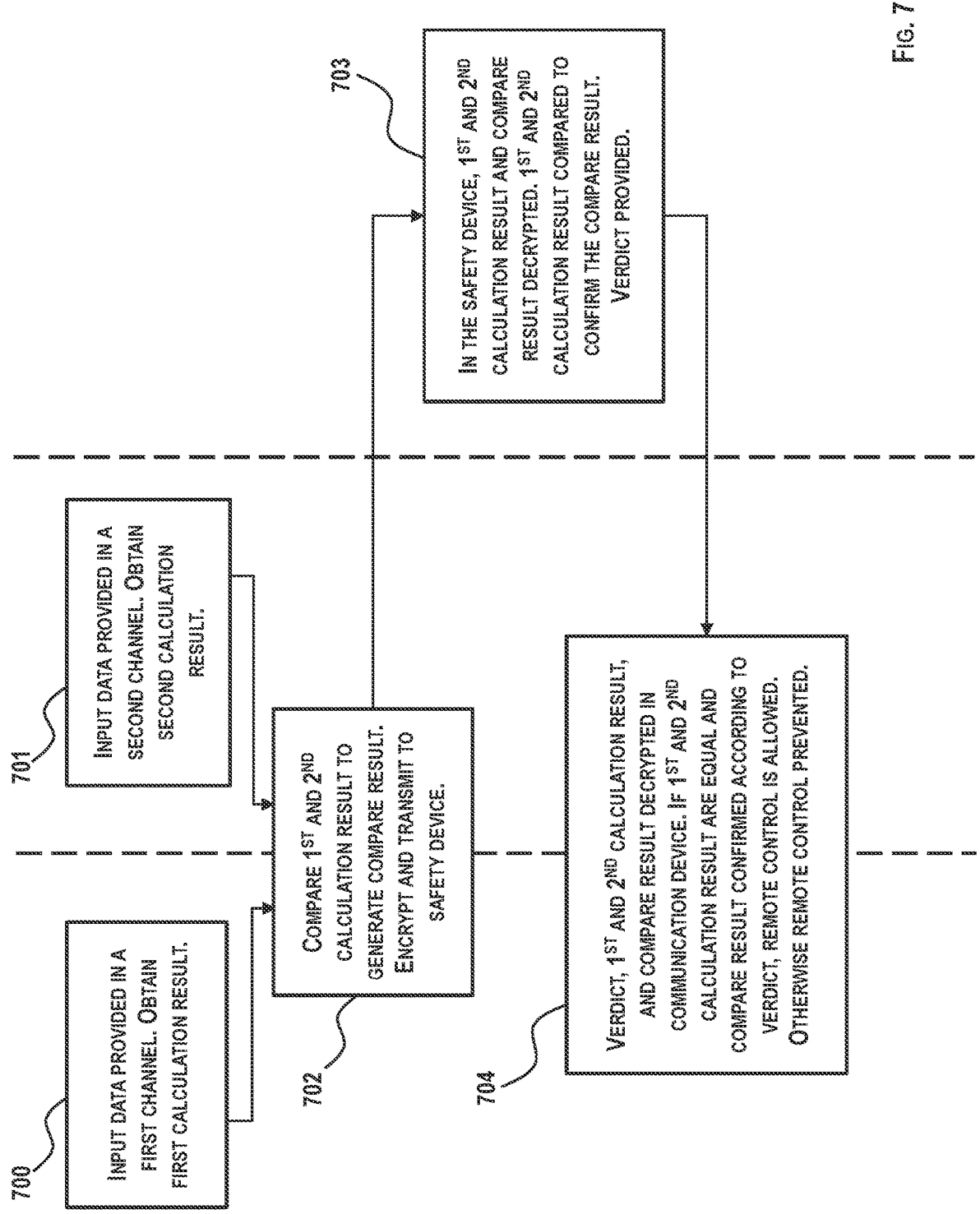
FIG. 7 is a flow diagram for steps of a further method for controlling operation of a medical device in a medical system.

FIG. 7 shows steps of a further embodiment of a method for controlling operation of a medical device 100 in a medical system further comprising a communication device 101 and a safety device 102. In step 700, input data is provided in a first channel of a medical device application running on a communication device 101, the medical device application adapted for remote operation control of the medical device 100. The input data is processed in the first channel in a first calculation process resulting in first calculation result data. In step 701 the input data is provided in a second channel of the medical device application, the second channel being separate from the first channel. For example, the first channel and the second channel may employ different hardware of the communication device 101 and use different methodology to perform the same calculations in the medical device application. The input data is processed in the second channel in a second calculation process resulting in second calculation result data in step 701. Steps 700 and 701 may be performed in any order or, at least partially, in parallel.

In step 702, the first and second calculation result data are compared resulting in compare result data (or "compare result") indicative of the result of comparing the first and second calculation result data. The first calculation result data, the second calculation result data and the compare result data are encrypted and transmitted to the safety device 102. Additionally, the input data may be encrypted and transmitted to the safety device 102.

In step 703, in the safety device 102, the first calculation result data, the second calculation result data and the compare result data are decrypted and the first and second calculation result data are compared to confirm the compare result data. Additionally, the input data may be decrypted and further confirmation functions may be executed. For example, third calculation result data may be generated by processing the input data in the safety device 102 in a third calculation process and the third calculation result data may be compared to the first and/or the second calculation result data to confirm the compare result data. Verdict data indicative of confirmation of the compare result data or failure to confirm the compare result data is provided in the safety device 102. The verdict data, the first calculation result data, the second calculation result data and the compare result data are encrypted and transmitted to the communication device 101.

The verdict data, the first calculation result data, the second calculation result data and the compare result data are decrypted in the communication device 101 in step 704. If the first and second calculation result data are found equal and the compare result data is confirmed according to the verdict data, remote control operation of the medical device 100 by the communication device 101 is allowed. If the first and second calculation result data are found not equal and/or the compare result data is not confirmed according to the verdict data, remote control operation of the medical device 100 by the communication device 101 is prevented in step 704.

FIG. 8 illustrates a self-test procedure in a method for controlling operation of a medical device 100 in a medical system further comprising a communication device 101 and a safety device 102. In step 800, first random data is created in a first channel of a medical device application running on a communication device 101, the medical device application adapted for remote operation control of the medical device 100. In step 801, second random data is created in a second channel of the medical device application, the second channel being separate from the first channel. Steps 800 and 801 may be performed in any order or, at least partially, in parallel.

In step 802, the first and second random data are compared resulting in compare result data indicative of the result of comparing the first and second random data. The first random data, the second random data and the compare result data are encrypted and transmitted to the safety device 102.

In step 803, in the safety device 102, the first random data, the second random data and the compare result data are decrypted and the first and second random data are compared to confirm the compare result data. Verdict data indicative of confirmation of the compare result data or failure to confirm the compare result data is provided in the safety device 102. The verdict data, the first random data, the second random data and the compare result data are encrypted and transmitted to the communication device 101.

The verdict data, the first random data, the second random data and the compare result data are decrypted in the communication device 101 in step 804. If the compare result data is confirmed according to the verdict data, remote control operation of the medical device 100 by the communication device 101 is allowed. If the compare result data is not confirmed according to the verdict data, remote control operation of the medical device 100 by the communication device 101 is prevented in step 804.

Embodiments of the methods described above with reference to FIGS. 4 to 8 may apply accordingly to a safety device 201 provided as an integrated device of a medical device 200.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

What is claimed is:

1. A method for controlling operation of a medical device in a medical system having a medical device, a communication device including a remote control for the medical device, and a safety device adapted for data communication with the communication device, the method comprising:
providing input data;
processing the input data by a first calculation in the communication device to thereby provide a first calculation result;
processing the input data by a second calculation executed separately from first calculation to thereby provide a second calculation result;
comparing the first and second calculation results;
when the first and second calculation results are found equal, allowing remote control of the medical device by a medical device application running on the communication device; and
when the first and second calculation results are found not equal, preventing the medical device application running on the communication device from remotely controlling the medical device.

2. The method according to claim 1, further comprising:
providing the input data in both the communication device and the safety device; and
processing the input data by the second calculation in the safety device.

3. The method according to claim 2, further comprising:
receiving the input data in a first component of the communication device and the safety device;
encrypting the input data in the first component;
transmitting the encrypted input data from the first component to a second component of the communication device and the safety device; and
decrypting the encrypted input data in the second component.

4. The method according to claim 2, further comprising:
encrypting the first calculation result in the communication device;
transmitting the encrypted first calculation result from the communication device to the safety device; and
decrypting the encrypted first calculation result in the safety device.

5. The method according to claim 1, further comprising:
providing the input data in the communication device; and
processing the input data in the second calculation in the communication device.

6. The method according to claim 5, further comprising:
encrypting the first and second calculation results in the communication device;
transmitting the encrypted first and second calculation results from the communication device to the safety device; and
decrypting the encrypted first and second calculation results in the safety device.

7. The method according to claim 1, further comprising:
providing the first and second calculation results in the safety device; and
comparing the first and second calculation results in the safety device.

8. The method according to claim 7, further comprising:
providing compare result data in the safety device, the compare result data indicative of the result of comparing the first and second calculation results; and
transmitting the compare result data from the safety device to the communication device.

9. The method according to claim 7, further comprising:
encrypting the first calculation result in the communication device;
transmitting the encrypted first calculation result from the communication device to the safety device; and
decrypting the encrypted first calculation result in the safety device.

10. The method according to claim 1, further comprising comparing the first and second calculation results in the communication device.

11. The method according to claim 10, further comprising:
encrypting the second calculation result in the safety device;
transmitting the encrypted second calculation result from the safety device to the communication device; and
decrypting the encrypted second calculation result in the communication device.

12. The method according to claim 1, further comprising selecting the safety device from the following group: memory card, SD card, NFC beacon, remote server device, further medical device different from the medical device.

13. The method according to claim 1, further comprising providing the first and second calculations and the comparing of the first and second calculation results as safety elements of a single fault safety architecture.

14. The method according to claim 1, further comprising storing, in a memory provided in at least one of the communication device and the safety device, at least one of the following: the input data; the encrypted input data; the first calculation result; the encrypted first calculation result; the second calculation result; and the encrypted second calculation result.

15. A medical system, comprising:
a medical device;
a communication device provided with a medical device application configured to run on the communication device and adapted for remote control of the medical device; and
a safety device adapted for data communication with the communication device; wherein the system is configured to:
provide input data;
process the input data by a first calculation in the communication device to thereby provide a first calculation result;
process the input data by a second calculation executed separately from the first calculation to thereby provide a second calculation result;
compare the first and second calculation results;
when the first and second calculation results are found equal, allow remote control of the medical device by a medical device application running on the communication device; and
when the first and second calculation results are found not equal, prevent the medical device application running on the communication device from remotely controlling the medical device.

* * * * *